United States Patent
Wagner et al.

(10) Patent No.: US 9,724,202 B2
(45) Date of Patent: *Aug. 8, 2017

(54) FEMORAL COMPONENT OF A KNEE PROSTHESIS HAVING AN ANGLED CEMENT POCKET

(71) Applicant: DEPUY IRELAND UNLIMITED COMPANY, Cork (IE)

(72) Inventors: Christel M. Wagner, Plymouth, IN (US); Joseph G. Wyss, Fort Wayne, IN (US); David S. Barrett, Awbridge (GB)

(73) Assignee: DEPUY IRELAND UNLIMITED COMPANY, Co Cork (IE)

(*) Notice: Subject to any disclaimer, the term of this patent is extended or adjusted under 35 U.S.C. 154(b) by 50 days.

This patent is subject to a terminal disclaimer.

(21) Appl. No.: 14/482,227

(22) Filed: Sep. 10, 2014

(65) Prior Publication Data
US 2014/0379091 A1    Dec. 25, 2014

Related U.S. Application Data

(63) Continuation of application No. 13/672,229, filed on Nov. 8, 2012, now Pat. No. 8,845,746, which is a
(Continued)

(51) Int. Cl.
*A61F 2/38* (2006.01)
*A61F 2/46* (2006.01)
*A61F 2/30* (2006.01)

(52) U.S. Cl.
CPC .......... *A61F 2/3859* (2013.01); *A61F 2/38* (2013.01); *A61F 2/389* (2013.01); *A61F 2/3836* (2013.01); *A61F 2/3868* (2013.01); *A61F 2/3886* (2013.01); *A61F 2002/30322* (2013.01); *A61F 2002/30449* (2013.01); *A61F 2002/30772* (2013.01); *A61F 2002/30878* (2013.01); *A61F 2002/30884* (2013.01); *A61F 2002/30889* (2013.01);
(Continued)

(58) Field of Classification Search
None
See application file for complete search history.

(56) References Cited

U.S. PATENT DOCUMENTS 3,965,490 A    6/1976  Murray et al.
4,530,116 A    7/1985  Frey
(Continued)

FOREIGN PATENT DOCUMENTS

CN    101522137 A    9/2009
DE    102004056713 A1    6/2006
(Continued)

OTHER PUBLICATIONS

European Search Report, European Patent Application No. 11175834.8-2310, Jan. 16, 2012, 7 pages.
(Continued)

*Primary Examiner* — Thomas J Sweet
*Assistant Examiner* — Megan Wolf
(74) *Attorney, Agent, or Firm* — Barnes & Thornburg LLP

(57) ABSTRACT

An implantable orthopedic knee prosthesis includes a component that is configured to be coupled to a surgically-prepared bone. A fixation side of the component includes a fixation surface that has an angled cement pocket formed therein.

14 Claims, 8 Drawing Sheets

Related U.S. Application Data continuation of application No. 13/249,496, filed on Sep. 30, 2011, now Pat. No. 8,317,870, which is a continuation-in-part of application No. 12/894,651, filed on Sep. 30, 2010, now Pat. No. 8,287,601.

(52) U.S. Cl.
    CPC .......... *A61F 2002/3895* (2013.01); *A61F 2002/4631* (2013.01)

(56) References Cited

U.S. PATENT DOCUMENTS

| | | |
|---|---|---|
| 4,808,185 A | 2/1989 | Penenberg et al. |
| 4,938,769 A | 7/1990 | Shaw |
| 4,944,760 A | 7/1990 | Kenna |
| 4,963,152 A | 10/1990 | Hofmann et al. |
| 5,037,423 A | 8/1991 | Kenna |
| 5,108,442 A | 4/1992 | Smith |
| 5,171,276 A | 12/1992 | Caspari et al. |
| 5,201,768 A | 4/1993 | Caspari et al. |
| 5,207,711 A | 5/1993 | Caspari et al. |
| 5,326,361 A | 7/1994 | Hollister |
| 5,330,534 A | 7/1994 | Herrington et al. |
| 5,336,266 A | 8/1994 | Caspari et al. |
| 5,344,460 A | 9/1994 | Turanyi et al. |
| 5,344,461 A | 9/1994 | Phlipot |
| 5,458,637 A | 10/1995 | Hayes |
| 5,509,934 A | 4/1996 | Cohen |
| 5,658,344 A | 8/1997 | Hurlburt |
| 5,683,472 A | 11/1997 | O'Neil et al. |
| 5,690,636 A | 11/1997 | Wildgoose et al. |
| 5,702,447 A | 12/1997 | Walch et al. |
| 5,702,463 A | 12/1997 | Pothier et al. |
| 5,702,464 A | 12/1997 | Lackey et al. |
| 5,755,803 A | 5/1998 | Haines |
| 5,755,808 A | 5/1998 | DeCarlo et al. |
| 5,766,257 A | 6/1998 | Goodman et al. |
| 5,800,546 A | 9/1998 | Marik et al. |
| 5,879,387 A | 3/1999 | Jones et al. |
| 5,906,644 A | 5/1999 | Powell |
| 5,951,564 A | 9/1999 | Schroder et al. |
| 5,951,603 A | 9/1999 | O'Neil et al. |
| 5,976,147 A | 11/1999 | LaSalle et al. |
| 5,997,577 A | 12/1999 | Herrington et al. |
| 6,010,534 A | 1/2000 | O'Neil et al. |
| 6,053,945 A | 4/2000 | O'Neil et al. |
| 6,059,831 A * | 5/2000 | Braslow .......... A61B 17/154 128/898 |
| 6,123,728 A | 9/2000 | Brosnahan |
| 6,126,692 A | 10/2000 | Robie et al. |
| 6,139,581 A | 10/2000 | Engh et al. |
| 6,179,876 B1 | 1/2001 | Stamper et al. |
| 6,224,632 B1 | 5/2001 | Pappas et al. |
| 6,344,059 B1 | 2/2002 | Krakovits et al. |
| 6,428,577 B1 | 8/2002 | Evans et al. |
| 6,485,519 B2 | 11/2002 | Meyers et al. |
| 6,494,914 B2 | 12/2002 | Brown et al. |
| 6,503,280 B2 | 1/2003 | Repicci |
| 6,569,202 B2 | 5/2003 | Whiteside |
| 6,620,198 B2 | 9/2003 | Burstein et al. |
| 6,645,251 B2 | 11/2003 | Salehi et al. |
| 6,652,592 B1 | 11/2003 | Grooms et al. |
| 6,660,039 B1 | 12/2003 | Evans et al. |
| 6,679,917 B2 | 1/2004 | Ek |
| 6,716,249 B2 | 4/2004 | Hyde |
| 6,719,800 B2 | 4/2004 | Meyers et al. |
| 6,726,724 B2 | 4/2004 | Repicci |
| 6,773,461 B2 | 8/2004 | Meyers et al. |
| 6,783,548 B2 | 8/2004 | Hyde, Jr. |
| 6,869,448 B2 | 3/2005 | Tuke et al. |
| 6,875,235 B2 | 4/2005 | Ferree |
| 6,923,832 B1 | 8/2005 | Sharkey et al. |
| 6,942,670 B2 | 9/2005 | Heldreth et al. |
| 6,953,479 B2 | 10/2005 | Carson et al. |
| 6,984,248 B2 | 1/2006 | Hyde, Jr. |
| 6,994,730 B2 | 2/2006 | Posner |
| 7,025,788 B2 | 4/2006 | Metzger et al. |
| 7,048,741 B2 | 5/2006 | Swanson |
| 7,070,622 B1 | 7/2006 | Brown et al. |
| 7,077,867 B1 | 7/2006 | Pope et al. |
| 7,087,082 B2 | 8/2006 | Paul et al. |
| 7,104,996 B2 * | 9/2006 | Bonutti .......... A61B 17/025 606/86 R |
| 7,108,720 B2 | 9/2006 | Hanes |
| 7,208,013 B1 | 4/2007 | Bonutti |
| 7,255,715 B2 | 8/2007 | Metzger |
| 7,278,997 B1 | 10/2007 | Mueller et al. |
| 7,294,149 B2 | 11/2007 | Hozack et al. |
| 7,297,164 B2 | 11/2007 | Johnson et al. |
| 7,341,602 B2 | 3/2008 | Fell et al. |
| 7,357,817 B2 | 4/2008 | D'Alessio, II |
| 7,445,639 B2 | 11/2008 | Metzger et al. |
| 7,494,507 B2 | 2/2009 | Dixon et al. |
| 7,497,874 B1 | 3/2009 | Metzger et al. |
| 7,527,650 B2 | 5/2009 | Johnson et al. |
| 7,563,286 B2 | 7/2009 | Gerber et al. |
| 7,572,295 B2 | 8/2009 | Steinberg |
| 7,578,850 B2 | 8/2009 | Kuczynski et al. |
| 7,608,079 B1 | 10/2009 | Blackwell et al. |
| 7,611,519 B2 | 11/2009 | Lefevre et al. |
| 7,618,462 B2 | 11/2009 | Ek |
| 7,628,817 B1 | 12/2009 | Axelson, Jr. et al. |
| 7,628,818 B2 | 12/2009 | Hazebrouck et al. |
| 7,635,390 B1 | 12/2009 | Bonutti |
| 7,678,151 B2 | 3/2010 | Ek |
| 7,678,152 B2 | 3/2010 | Suguro et al. |
| 7,695,519 B2 | 4/2010 | Collazo |
| 7,740,662 B2 | 6/2010 | Barnett et al. |
| 7,748,984 B2 | 7/2010 | McAllister et al. |
| 7,749,229 B1 | 7/2010 | Bonutti |
| 7,753,960 B2 | 7/2010 | Cipolletti et al. |
| 7,758,653 B2 | 7/2010 | Steinberg |
| 7,766,911 B1 | 8/2010 | Navarro et al. |
| 7,776,044 B2 | 8/2010 | Pendleton et al. |
| 7,780,666 B1 | 8/2010 | Navarro et al. |
| 7,785,327 B1 | 8/2010 | Navarro et al. |
| 7,790,779 B2 | 9/2010 | Muratoglu |
| 7,803,193 B2 | 9/2010 | Steinberg |
| 7,833,245 B2 | 11/2010 | Kaes et al. |
| 2003/0014122 A1 | 1/2003 | Whiteside |
| 2003/0220697 A1 | 11/2003 | Justin et al. |
| 2003/0225456 A1 | 12/2003 | Ek |
| 2004/0019384 A1 | 1/2004 | Kirking et al. |
| 2004/0039450 A1 | 2/2004 | Griner et al. |
| 2005/0015153 A1 | 1/2005 | Goble et al. |
| 2005/0125068 A1 | 6/2005 | Hozack et al. |
| 2006/0030945 A1 | 2/2006 | Wright |
| 2006/0047283 A1 | 3/2006 | Evans et al. |
| 2006/0100714 A1 | 5/2006 | Ensign |
| 2006/0111790 A1 | 5/2006 | Dietz |
| 2007/0010890 A1 | 1/2007 | Collazo |
| 2007/0061014 A1 | 3/2007 | Naegerl |
| 2007/0100463 A1 | 5/2007 | Aram et al. |
| 2007/0162143 A1 | 7/2007 | Wasielewski |
| 2007/0162144 A1 | 7/2007 | Wasielewski |
| 2007/0219639 A1 | 9/2007 | Otto et al. |
| 2008/0004708 A1 | 1/2008 | Wyss |
| 2008/0021567 A1 | 1/2008 | Meulink et al. |
| 2008/0097615 A1 | 4/2008 | Lipman et al. |
| 2008/0097616 A1 | 4/2008 | Meyers et al. |
| 2008/0114462 A1 | 5/2008 | Guidera et al. |
| 2008/0114464 A1 | 5/2008 | Barnett et al. |
| 2008/0119940 A1 | 5/2008 | Otto et al. |
| 2008/0133019 A1 | 6/2008 | Andrysek |
| 2008/0195108 A1 | 8/2008 | Bhatnagar et al. |
| 2009/0048680 A1 | 2/2009 | Naegerl |
| 2009/0082873 A1 | 3/2009 | Hazebrouck et al. |
| 2009/0088859 A1 | 4/2009 | Hazebrouck et al. |
| 2009/0125114 A1 | 5/2009 | May et al. |
| 2009/0125115 A1 | 5/2009 | Popoola et al. |
| 2009/0264894 A1 | 10/2009 | Wasielewski |
| 2009/0265012 A1 | 10/2009 | Engh et al. |
| 2009/0265013 A1 | 10/2009 | Mandell |

(56) References Cited

U.S. PATENT DOCUMENTS

| | | |
|---|---|---|
| 2009/0295035 A1 | 12/2009 | Evans |
| 2009/0326663 A1 | 12/2009 | Dun |
| 2009/0326664 A1 | 12/2009 | Wagner et al. |
| 2009/0326665 A1 | 12/2009 | Wyss et al. |
| 2009/0326666 A1 | 12/2009 | Wyss et al. |
| 2009/0326667 A1 | 12/2009 | Williams et al. |
| 2010/0016979 A1 | 1/2010 | Wyss et al. |
| 2010/0036499 A1 | 2/2010 | Pinskerova |
| 2010/0036500 A1 | 2/2010 | Heldreth et al. |
| 2010/0042224 A1 | 2/2010 | Otto et al. |
| 2010/0042225 A1 | 2/2010 | Shur |
| 2010/0070045 A1 | 3/2010 | Ek |
| 2010/0076563 A1 | 3/2010 | Otto et al. |
| 2010/0076564 A1 | 3/2010 | Schilling et al. |
| 2010/0094429 A1 | 4/2010 | Otto |
| 2010/0100189 A1 | 4/2010 | Metzger |
| 2010/0100190 A1 | 4/2010 | May et al. |
| 2010/0100191 A1 | 4/2010 | May et al. |
| 2010/0114322 A1 | 5/2010 | Clifford et al. |
| 2010/0125337 A1 | 5/2010 | Grecco et al. |
| 2010/0161067 A1 | 6/2010 | Saleh et al. |
| 2010/0191341 A1 | 7/2010 | Byrd |
| 2010/0222890 A1 | 9/2010 | Barnett et al. |
| 2010/0262144 A1 | 10/2010 | Kelman et al. |
| 2010/0286788 A1 | 11/2010 | Komistek |
| 2010/0292804 A1 | 11/2010 | Samuelson |
| 2010/0305710 A1 | 12/2010 | Metzger et al. |
| 2010/0312350 A1 | 12/2010 | Bonutti |

FOREIGN PATENT DOCUMENTS

| | | |
|---|---|---|
| EP | 0941719 A2 | 9/1999 |
| EP | 1186277 A2 | 10/2005 |
| EP | 2042131 A2 | 4/2009 |
| JP | 10137271 A | 5/1998 |
| JP | 2002315757 A | 10/2002 |
| WO | 0051528 A1 | 9/2000 |
| WO | 03099106 A2 | 12/2003 |
| WO | 2005082039 A2 | 9/2005 |
| WO | 2008048820 A2 | 4/2008 |
| WO | 2010039963 A1 | 4/2010 |
| WO | 2010056962 A1 | 5/2010 |

OTHER PUBLICATIONS

European Search Report, European Patent Application No. 12186701.4-2310, Dec. 12, 2012, 5 pages.

First Office Action issued by the State Intellectual Property Office of China on Dec. 2, 2014 for Chinese Patent Application No. 201110309763.0, 3 pages.

* cited by examiner

FEMORAL COMPONENT OF A KNEE PROSTHESIS HAVING AN ANGLED CEMENT POCKET

This application is a continuation of U.S. application Ser. No. 13/672,229, which was filed on Nov. 8, 2012 and was a continuation of U.S. application Ser. No. 13/249,496, now U.S. Pat. No. 8,317,870, which was a continuation-in-part of U.S. application Ser. No. 12/864,651, now U.S. Pat. No. 8,287,601, the entirety of each of which is hereby incorporated by reference.

TECHNICAL FIELD

The present disclosure relates generally to an implantable orthopaedic prosthesis, and more particularly to an implantable knee prosthesis.

BACKGROUND

During the lifetime of a patient, it may be necessary to perform a joint replacement procedure on the patient as a result of, for example, disease or trauma. The joint replacement procedure may involve the use of a prosthesis which is implanted into one or more of the patient's bones. In the case of a knee replacement procedure, a tibial tray is implanted into the patient's tibia. A bearing is secured to the tibial tray. The condyle surfaces of a replacement femoral component bear against the tibial bearing.

During implantation of the femoral component, the surgeon typically preloads bone cement on the bone-contacting surfaces of the component. The preloaded bone cement has a tendency to escape the femoral component as it is positioned on the surgically-prepared distal femur. Advancement of the femoral component through escaped bone cement is referred to as "cement plowing". Both the escaped bone cement and the associated cement plowing lead to the performance of additional surgical steps to remove the extraneous bone cement prior to completion of the surgical procedure.

SUMMARY

According to one aspect, an implantable orthopaedic knee prosthesis includes a femoral component that is configured to be coupled to a surgically-prepared distal femur. The femoral component has an articular side that includes a posterior femoral condyle surface. A fixation side is opposite the articular side, and it includes a posterior fixation surface that extends generally in the superior/inferior direction. The posterior fixation surface has a posterior cement pocket formed therein that is deeper at its inferior end than at its superior end.

The fixation side of the femoral component may also include a distal fixation surface that extends generally in the anterior/posterior direction and a posterior-chamfer fixation surface that extends superiorly and posteriorly from the distal fixation surface in the direction toward the posterior fixation surface. The posterior-chamfer surface may have a posterior-chamfer cement pocket formed therein that is contiguous with the posterior cement pocket. Similarly, the distal fixation surface may have a distal cement pocket formed therein that is contiguous with the posterior-chamfer cement pocket.

The posterior cement pocket may be deeper at its inferior end than both the posterior-chamfer cement pocket and the distal cement pocket.

The fixation side of the femoral component may also include an anterior fixation surface that extends generally in the superior/inferior direction, and an anterior-chamfer fixation surface that extends superiorly and anteriorly from the distal fixation surface in the direction toward the anterior fixation surface. The anterior-chamfer surface may have an anterior-chamfer cement pocket formed therein that is contiguous with the distal cement pocket. The anterior fixation surface may include an anterior cement pocket formed therein that is contiguous with the anterior-chamfer cement pocket.

In an embodiment, the posterior cement pocket is deeper at its inferior end than both the anterior-chamfer cement pocket and the anterior cement pocket.

In an embodiment, the posterior fixation surface includes a mounting rim having a sidewall extending posteriorly therefrom. The sidewall defines the perimeter of the posterior cement pocket. When viewed sagittally, an inferior end of the sidewall is wider than a superior end of the sidewall.

According to another aspect, an implantable orthopaedic knee prosthesis includes a femoral component configured to be coupled to a surgically-prepared distal femur. The femoral component may include an articular side having a posterior femoral condyle surface, and a fixation side that is opposite the articular side. The fixation side may include a posterior fixation surface that extends generally in the superior/inferior direction. The posterior fixation surface may include a peripheral rim, a bottom wall spaced apart posteriorly from the peripheral rim, and a sidewall extending posteriorly from the posterior rim to the bottom wall. When viewed sagittally, an imaginary plane defined by the peripheral rim forms an acute angle with an imaginary plane defined by the bottom wall.

When viewed sagittally, an inferior end of the sidewall may be wider than a superior end of the sidewall.

In an embodiment, the sidewall and the bottom wall collectively define a cement pocket.

The articular side may include a posterior lateral femoral condyle surface. The articular side may also include a posterior medial femoral condyle surface.

According to another aspect, an implantable orthopaedic knee prosthesis includes a tibial tray configured to be coupled to a surgically-prepared proximal tibia and a bearing coupled to the tibial tray. The bearing includes a medial articular surface and a lateral articular surface. The knee prosthesis may also include a femoral component configured to be coupled to a surgically-prepared distal femur. The femoral component may include a lateral condyle surface configured to articulate with the lateral articular surface of the bearing and a medial condyle configured to articulate with the medial articular surface of the bearing. The femoral component may also include a posterior lateral fixation surface opposite the lateral condyle surface, with the posterior lateral fixation surface extending in the superior/inferior direction. The femoral component also includes a posterior medial fixation surface opposite the medial condyle surface, with the posterior medial fixation surface extending in the superior/inferior direction. Both the posterior medial fixation surface and the posterior lateral fixation surface may include a peripheral rim, a bottom wall spaced apart posteriorly from the peripheral rim, and a sidewall extending posteriorly from the posterior rim to the bottom wall. When viewed sagittally, an imaginary plane defined by the peripheral rim forms an acute angle with an imaginary plane defined by the bottom wall.

When viewed sagittally, an inferior end of the sidewall of the posterior medial fixation surface is wider than its superior end.

When viewed sagittally, an inferior end of the sidewall of the posterior lateral fixation surface is wider than its superior end.

The sidewall and the bottom wall of the posterior medial fixation surface collectively define a cement pocket.

The sidewall and the bottom wall of the posterior lateral fixation surface collectively also define a cement pocket.

According to another aspect, an implantable orthopaedic knee prosthesis includes a femoral component configured to be coupled to a surgically-prepared distal femur. The femoral component has an articular side that includes a femoral condyle surface and a fixation side that is opposite the articular side. The fixation side includes a fixation surface that extends generally in the superior/inferior direction. The fixation surface has a cement pocket formed therein that is deeper at its inferior end than at its superior end.

The fixation surface may include a mounting rim that has a sidewall extending therefrom. The sidewall defines the perimeter of the cement pocket. When viewed sagittally, the inferior end of the sidewall is wider than the superior end of the sidewall.

When viewed sagittally, an imaginary plane defined by the peripheral rim forms an acute angle with an imaginary plane defined by the bottom wall.

The fixation surface may include a posterior fixation surface having a posterior cement pocket formed therein. In such an arrangement, the bottom wall is spaced apart posteriorly from the peripheral rim, and the sidewall extends posteriorly from the posterior rim to the bottom wall.

The fixation surface may include an anterior fixation surface having an anterior cement pocket formed therein. In such an arrangement, the bottom wall is spaced apart anteriorly from the peripheral rim, and the sidewall extends anteriorly from the anterior rim to the bottom wall.

The femoral component may be embodied as a unicompartmental femoral component.

According to another aspect, an implantable orthopaedic knee prosthesis includes a tibial component configured to be coupled to a surgically-prepared proximal tibia. The tibial component includes a superior side, an inferior side that is opposite the superior side, and a fixation member extending inferiorly from the inferior side. The inferior side of the tibial component includes an inferior fixation surface that extends generally in the transverse plane, with such an inferior fixation surface having a posterior cement pocket formed therein. The posterior cement pocket is deeper at its anterior end than at its posterior end.

The implantable orthopaedic knee prosthesis may also include a tibial bearing component. In such a case, the tibial component may be embodied as a tibial tray, with the tibial bearing component being positioned on the tibial tray. The tibial tray may be metallic and the tibial bearing may be polymeric.

In other embodiments, the superior side of the tibial component may include a medial bearing surface configured to articulate with the medial condyle surface of a femoral component, and a lateral bearing surface configured to articulate with the lateral condyle surface of the femoral component. In such a case, the tibial component may be embodied as a monolithic polymeric component.

The inferior fixation surface of the tibial component may include a mounting rim having a sidewall extending superiorly therefrom. The sidewall defines the perimeter of the posterior cement pocket. When viewed sagittally, an anterior end of the sidewall is wider than a posterior end of the sidewall.

According to another aspect, an implantable orthopaedic knee prosthesis includes a tibial component configured to be coupled to a surgically-prepared proximal tibia. The tibial component includes a superior side, an inferior side that is opposite the superior side, and a fixation member extending inferiorly from the inferior side. The inferior side of the tibial component includes an inferior fixation surface that extends generally in the transverse plane. The inferior fixation surface includes a peripheral rim, a top wall spaced apart superiorly from the peripheral rim, and a sidewall extending superiorly from the posterior rim to the top wall. When viewed sagittally, an imaginary plane defined by the peripheral rim forms an acute angle with an imaginary plane defined by the top wall.

When viewed sagittally, an anterior end of the sidewall is wider than a posterior end of the sidewall.

The sidewall and the top wall collectively define a cement pocket.

The implantable orthopaedic knee prosthesis may also include a tibial bearing component. In such a case, the tibial component may be embodied as a tibial tray, with the tibial bearing component being positioned on the tibial tray. The tibial tray may be metallic and the tibial bearing may be polymeric.

In other embodiments, the superior side of the tibial component may include a medial bearing surface configured to articulate with the medial condyle surface of a femoral component, and a lateral bearing surface configured to articulate with the lateral condyle surface of the femoral component. In such a case, the tibial component may be embodied as a monolithic polymeric component.

According to another aspect, an implantable orthopaedic knee prosthesis includes a femoral component having a medial condyle surface and a lateral condyle surface. The implantable orthopaedic knee prosthesis also includes a bearing having a medial bearing surface configured to articulate with the medial condyle surface of the femoral component, and a lateral bearing surface configured to articulate with the lateral condyle surface of the femoral component. The implantable orthopaedic knee prosthesis further includes a tibial tray positioned below the bearing. The tibial tray includes a superior side, an inferior side that is opposite the superior side, and a fixation member extending inferiorly from the inferior side. The inferior side of the tibial tray includes an inferior fixation surface that extends generally in the transverse plane. The inferior fixation surface includes a peripheral rim, a top wall spaced apart superiorly from the peripheral rim, and a sidewall extending superiorly from the posterior rim to the top wall. When viewed sagittally, an imaginary plane defined by the peripheral rim forms an acute angle with an imaginary plane defined by the top wall.

When viewed sagittally, an anterior end of the sidewall is wider than a posterior end of the sidewall.

The sidewall and the top wall collectively define a cement pocket.

The tibial tray may be metallic and the tibial bearing may be polymeric.

In an embodiment the tibial bearing is rotatable relative to the tibial tray.

In another embodiment, the tibial bearing is fixed in position relative to the tibial tray.

BRIEF DESCRIPTION OF THE DRAWINGS

The detailed description particularly refers to the following figures, in which.

DETAILED DESCRIPTION OF THE DRAWINGS

Figure 1:
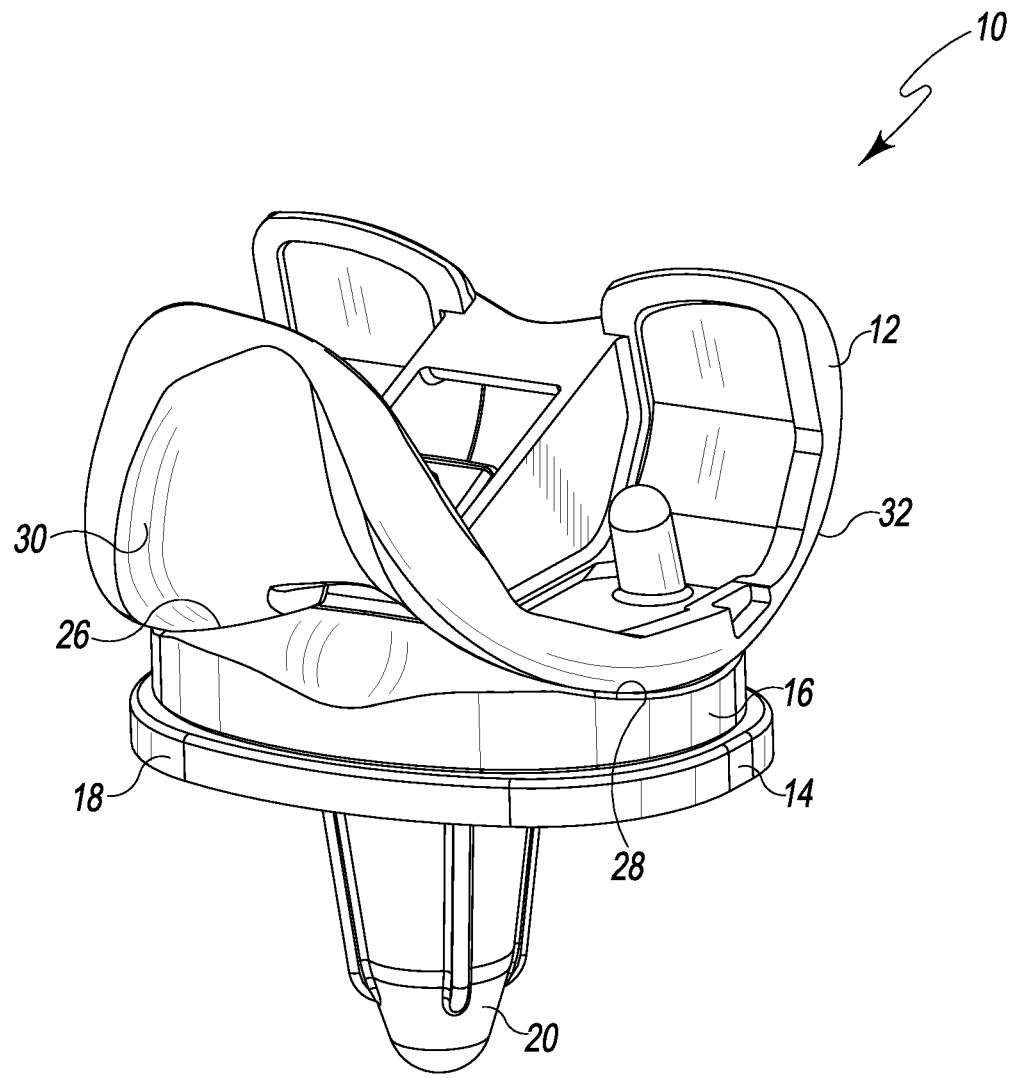
FIG. 1 is a perspective view of a knee prosthesis.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIGS. 1-5, there is shown a knee prosthesis 10. The knee prosthesis 10 includes a femoral component 12, a tibial tray 14, and a bearing 16. The femoral component 12 is configured to be secured to a surgically-prepared end of a patient's distal femur (not shown), whereas the tibial tray 14 is configured to be secured to a surgically-prepared end of a patient's proximal tibia (not shown).

The tibial tray 14 includes a platform 18 having a fixation member, such as an elongated stem 20, extending away from its lower surface. The bearing 16 includes a stem 22 (see FIG. 2) that is positionable within a complementary bore 24 (see FIG. 2) in the tibial tray 14. In such a way, the bearing 16 is free to rotate relative to the tibial tray 14. In other embodiments, the bearing 16 may be snap-fit or otherwise secured to the tibial tray 14. In such a way, the bearing 16 is fixed relative to the tibial tray 14 (i.e., it is not rotative or moveable in the anterior/posterior or medial/lateral directions). It should be appreciated that in such embodiments, other fixation members, such as one or more short pegs or posts, may be used in lieu of the elongated stem 20.

The bearing 16 includes a lateral articular surface 26 and a medial articular surface 28. The articular surfaces 26, 28 are configured to articulate with a lateral condyle surface 30 and a medial condyle surface 32, respectively, of the femoral component 12. Specifically, the femoral component 12 is configured to emulate the configuration of the patient's natural femoral condyles, and, as such, the lateral condyle surface 30 and the medial condyle surface 32 are configured (e.g., curved) in a manner which mimics the condyles of the natural femur. The lateral condyle surface 30 and the medial condyle surface 32 are spaced apart from one another thereby defining an intercondylar notch therebetween.

The components of the knee prosthesis 10 that engage the natural bone, such as the femoral component 12 and the tibial tray 14, may be constructed with a biocompatible metal, such as a cobalt chrome alloy, although other materials, such as ceramics, may also be used. The bone engaging surfaces of these components may be textured to facilitate cementing the component to the bone. Such surfaces may also be porous coated to promote bone ingrowth for permanent fixation.

The bearing 16 may be constructed with a material that allows for smooth articulation between the bearing 16 and the femoral component 12, such as a polymeric material. One such polymeric material is polyethylene such as ultra-high molecular weight polyethylene (UHMWPE), although other biocompatible polymers may be used.

Although the femoral component 12 is herein illustratively described as a monolithic component, it is characterized by a number of "regions" or "structures". For example, the anterior structure of the femoral component 12 is referred to as an anterior flange 34. The anterior flange 34 transitions to an anterior chamfer region 36, which, in turn, transitions to a distal condylar region 38. The distal condylar region 38 transitions to a posterior chamfer region 40. A pair of posterior femoral condyles 42 form the posterior structure of the femoral component 12.

Figure 2:
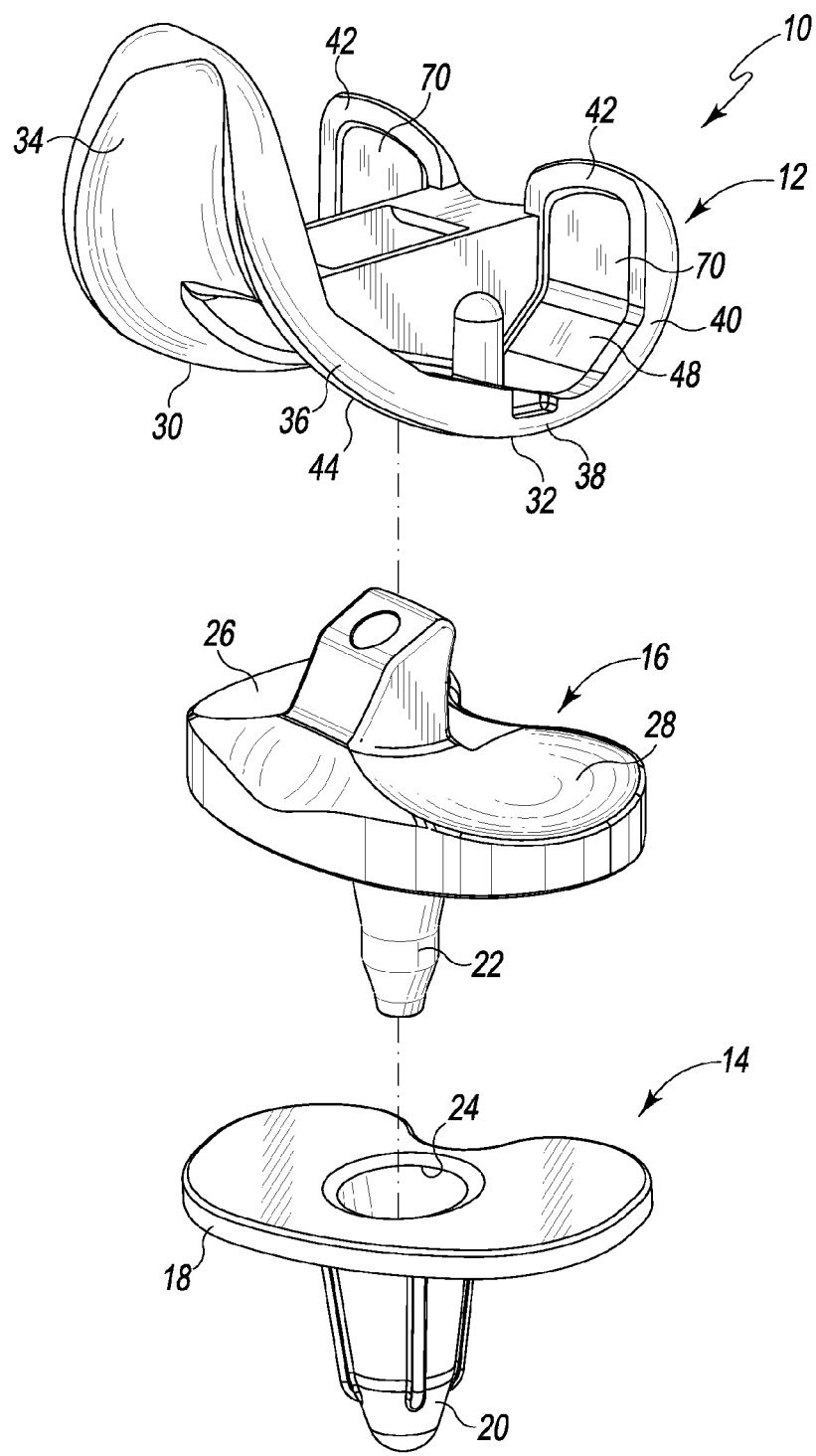
FIG. 2 is an exploded perspective view of the knee prosthesis of FIG. 1.
Figure 3:
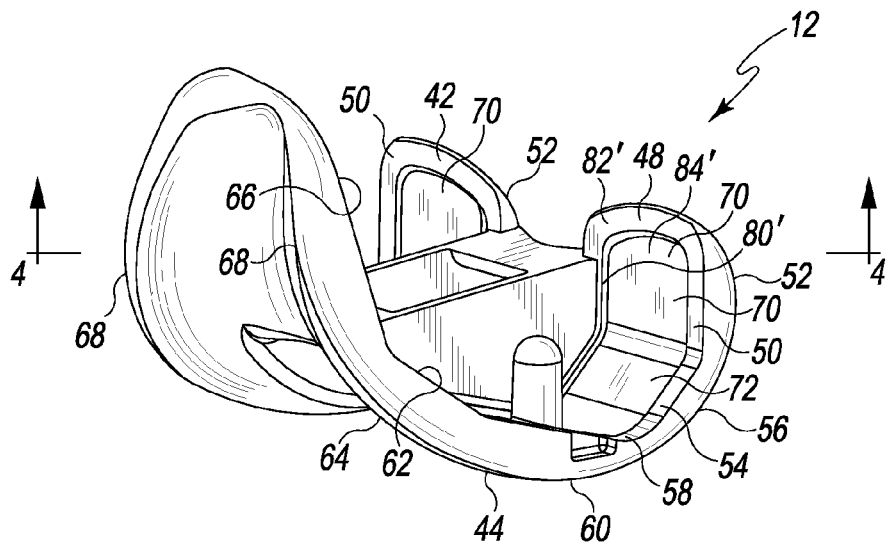
FIG. 3 is a perspective view of the femoral component of the knee prosthesis of FIG. 1.
Figure 4:
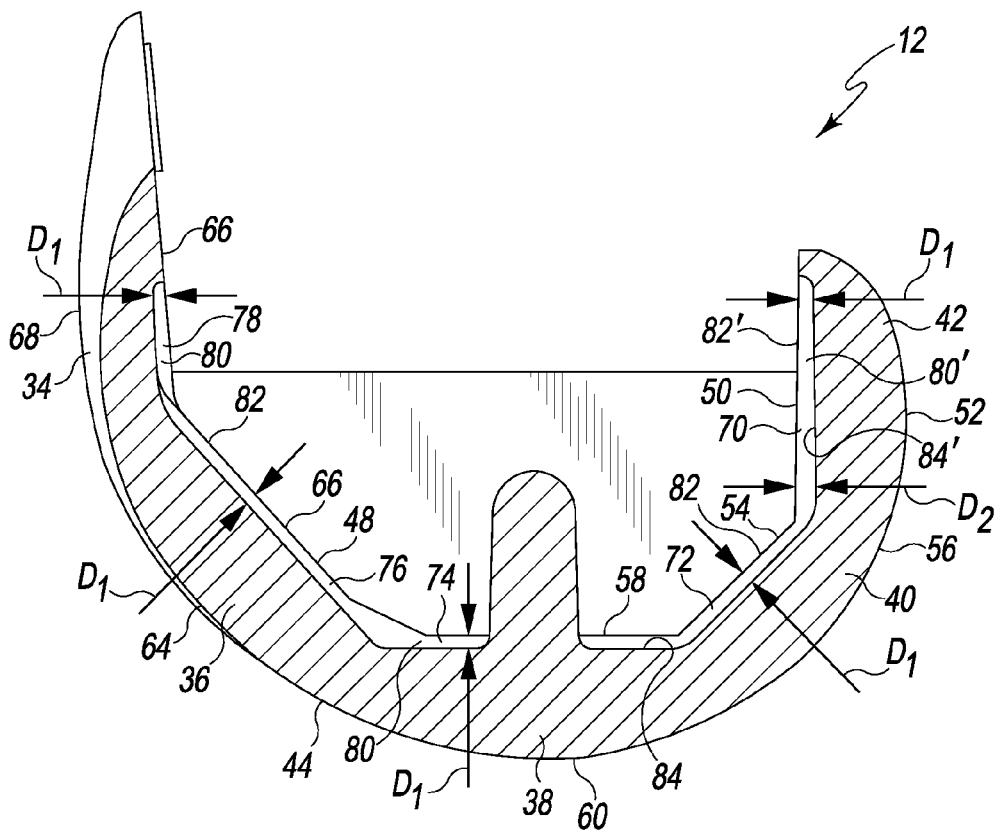
FIG. 4 is a sagittal cross section view of the femoral component of FIG. 3.

As shown in FIG. 2, both the lateral condyle surface 30 and the medial condyle surface 32 are formed in the articular side 44 of the femoral component 12. A fixation side 48 is opposite the articular side 44, and is the side of the femoral component 12 that contacts the surgically-prepared distal femur of the patient. The fixation side 48 includes multiple surfaces that mate with planar surfaces surgically cut into the patient's distal femur. Specifically, as shown in FIG. 3, a pair of posterior fixation surfaces 50 are opposite the posterior condyle surfaces 52, with one of the posterior fixation surfaces 50 being the medial fixation surface, the other the lateral fixation surface. As can be seen in FIG. 4, the posterior fixation surfaces 50 extend generally in the superior/inferior direction. A pair of distal fixation surfaces 58 (one being medially positioned, the other the laterally positioned) are opposite the distal condyle surfaces 60. The distal fixation surfaces 58 extend generally in the anterior/posterior direction. The medial and lateral posterior-chamfer fixation surfaces 54 are opposite the posterior-chamfer condyle surfaces 56. The medial and lateral posterior-chamfer fixation surfaces 54 extend superiorly and posteriorly from their respective medial and lateral distal fixation surfaces 58 in the direction toward their respective posterior fixation surfaces 50. The medial and lateral anterior-chamfer fixation surfaces 62 are opposite the anterior-chamfer condyle surfaces 64, respectively, and extend superiorly and anteriorly away from their respective distal fixation surfaces 58 in the direction toward an anterior fixation surface 66. The anterior fixation surface 66 is opposite the anterior condyle surface 68 and, like the posterior fixation surfaces 50, extends generally in the superior/inferior direction.

Each of the fixation surfaces has a cement pocket formed therein. In particular, a posterior cement pocket 70 is formed in each of the posterior fixation surfaces 50, a posterior-chamfer cement pocket 72 is formed in each of the posterior-chamfer fixation surfaces 54, a distal cement pocket 74 is formed in each of the distal fixation surfaces 58, an anterior-chamfer cement pocket 76 is formed in each of the anterior-chamfer fixation surfaces 62, and an anterior cement pocket 78 is formed in the anterior fixation surface 66. In the illustrative embodiment described herein, the adjacent cement pockets are contiguous with one another such that a single, continuous cement pocket is formed in the fixation side 48 of the femoral component.

Figure 5:
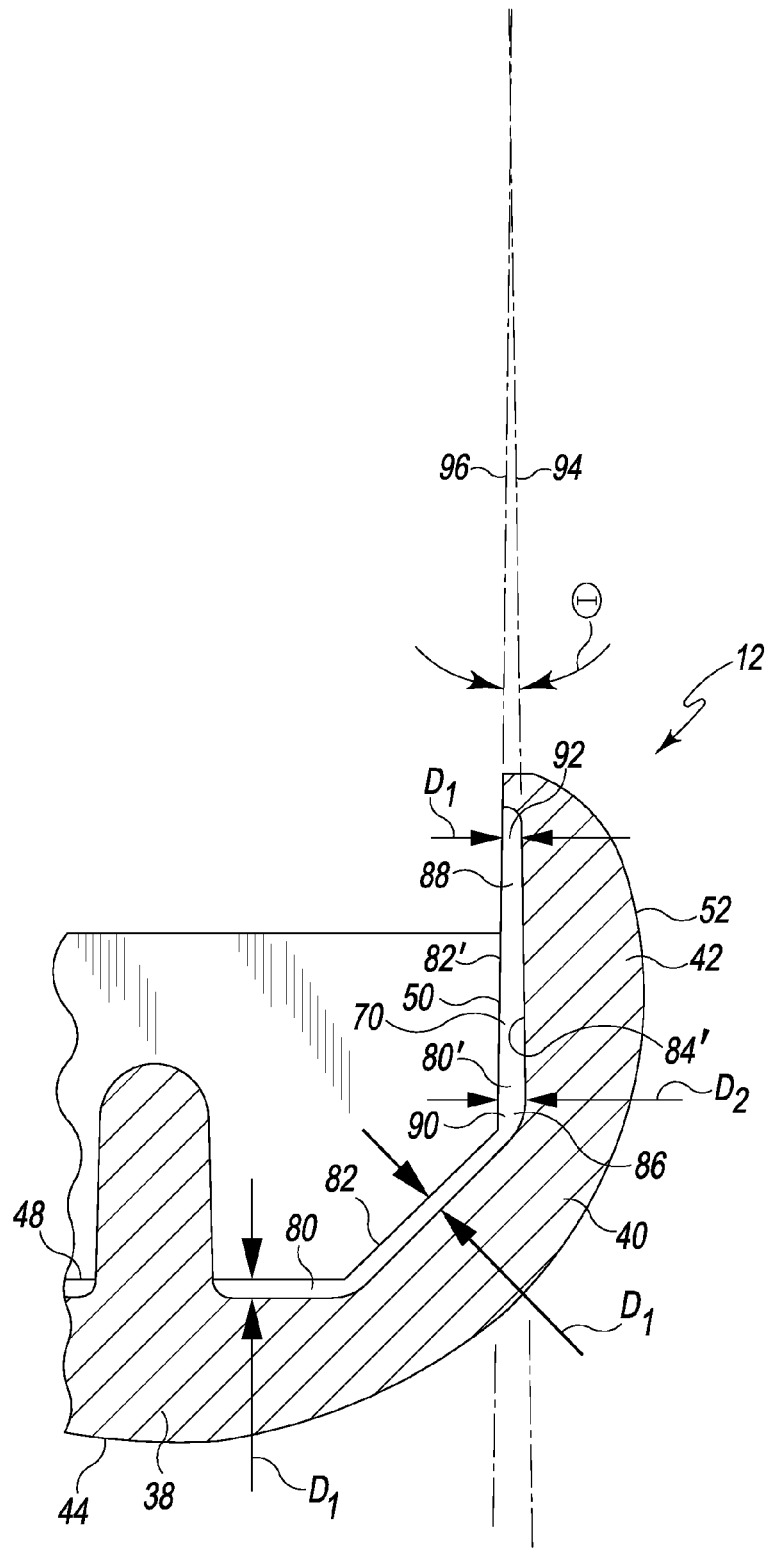
FIG. 5 is an enlarged, fragmentary view of a portion of FIG. 4 showing the posterior condyles of the femoral component in greater detail.

Each of the cement pockets 70, 72, 74, 76, 78 is formed by a sidewall 80 that extends away from a mounting rim 82. As can be seen in FIGS. 3-5, the sidewall 80 forms the perimeter of the respective cement pockets 70, 72, 74, 76, 78. A bottom wall 84 is spaced apart from the mounting rim 82 and is connected thereto by the sidewall 80. In such a way, the sidewall 80 and the bottom wall 84 collectively define the respective cement pockets 70, 72, 74, 76, 78.

The depth ($D_1$) of each of the posterior-chamfer cement pocket 72, the distal cement pocket 74, the anterior-chamfer cement pocket 76, and the anterior cement pocket 78 is approximately equal. In the illustrative embodiment described herein, each of the cement pockets 72, 74, 76, and 78 is approximately 1 mm deep (i.e., $D_1=1$ mm).

The posterior cement pocket 70, on the other hand, is angled and, as a result, is deeper at its inferior end than on its superior end. In particular, as shown in FIG. 5, the posterior cement pocket 70 is formed by a sidewall 80' that extends posteriorly from the mounting rim 82' of the posterior fixation surface 50 to the bottom wall 84'. When viewed sagittally, such as in the cross sectional view of FIGS. 4 and 5, the inferior end 86 of the sidewall 80' is wider than the superior end 88 of the sidewall 80'. As a result, the posterior cement pocket 70 is deeper at its inferior end 90 than at its superior end 92. In the illustrative embodiment described herein, the superior end 92 of the posterior cement pocket 70 has a depth that is greater than 0 mm (i.e., $D_1>0$ mm) and is approximately equal to the depth of the other cement pockets 72, 74, 76, and 78. In other words, the superior end 92 of the posterior cement pocket 70 is approximately 1 mm deep (i.e., $D_1=1$ mm). However, the inferior end 90 of the posterior cement pocket 70 is illustratively 1.5 mm deep (i.e., $D_2=1.5$ mm). It should be appreciated that other dimensions may also be used to fit the need of a given design of the femoral component 12.

Such an arrangement creates an angled bottom wall 84'. In particular, the bottom wall 84' slopes anteriorly from its inferior end 86 to its superior end 88. This sloped arrangement is illustratively shown in the cross sectional view of FIG. 5. As can be seen in that view, an imaginary plane 96 is defined by the mounting rim 82' of the posterior fixation surface 50, whereas the bottom wall 84' of the posterior fixation surface 50 defines an imaginary plane 94. The two imaginary planes 94, 96 form an acute angle (θ) therebetween. Such an acute angle is indicative of the slope of the bottom wall 84' relative to the mounting rim 82'.

During a surgical procedure to implant the femoral component 12 to the surgically-prepared distal end of the patient's femur, the cement pockets 70, 72, 74, 76, 78 are preloaded with bone cement. The femoral component 12 is then positioned on the patient's surgically-prepared distal femur, which has also been coated in bone cement. The angled arrangement of posterior cement pocket 70 hydraulically loads the bone cement within the cement pocket. This enhances containment of the bone cement and reduces the occurrences of cement plowing. The arrangement of the posterior cement pocket 70 also improves filling of the bone cement and pressurization which, in turn, leads to enhanced bonding of the femoral component 12 to the distal femur.

Figure 6:
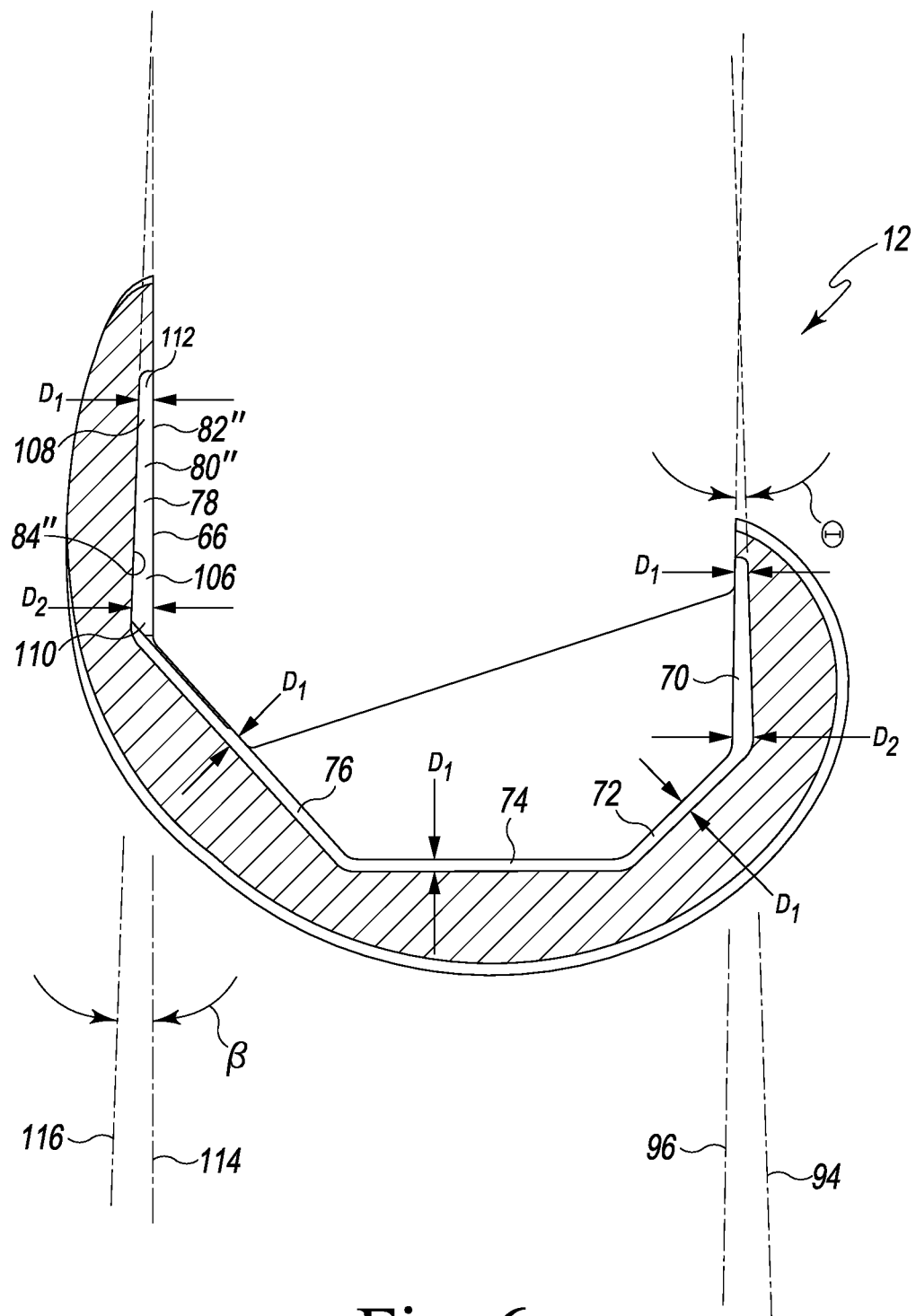
FIG. 6 is a view similar to FIG. 4, but showing another embodiment of the femoral component in which both the posterior and anterior cement pockets are angled.

Referring now to FIG. 6, another embodiment of the femoral component 12 is shown. In this embodiment, both the posterior cement pocket 70 and the anterior cement pocket 78 are angled. As such, both cement pockets 70, 78 are deeper at their respective inferior ends than at their respective superior ends. In the embodiment shown in FIG. 6, the posterior cement pocket 70 is essentially the same as discussed above in regard to FIGS. 1-5. As to the anterior cement pocket 78, it is formed by a sidewall 80" that extends anteriorly from the mounting rim 82" of the anterior fixation surface 66 to the bottom wall 84". When viewed sagittally, such as in the cross sectional view of FIG. 6, the inferior end 106 of the sidewall 80" is wider than the superior end 108 of the sidewall 80". As a result, like the posterior cement pocket 70, the anterior cement pocket 78 is deeper at its inferior end 110 than at its superior end 112. In the illustrative embodiment described herein, the superior end 112 of the anterior cement pocket 78 has a depth that is greater than 0 mm (i.e., $D_1>0$ mm) and is approximately equal to the depth of the other cement pockets 72, 74, and 76. In other words, the superior end 112 of the anterior cement pocket 70 is approximately 1 mm deep (i.e., $D_1=1$ mm). However, the inferior end 110 of the anterior cement pocket 78 is illustratively 1.5 mm deep (i.e., $D_2=1.5$ mm). It should be appreciated that other dimensions may also be used to fit the need of a given design of the femoral component 12.

Such an arrangement creates an angled bottom wall 84". In particular, the bottom wall 84" of the anterior cement pocket 78 slopes posteriorly from its inferior end 106 to its superior end 108. This sloped arrangement is illustratively shown in FIG. 6 in which an imaginary plane 114 is defined by the mounting rim 82" of the anterior fixation surface 66, whereas the bottom wall 84" of the anterior fixation surface 66 defines an imaginary plane 116. The two imaginary planes 114, 116 form an acute angle (β) therebetween. Such an acute angle is indicative of the slope of the bottom wall 84" relative to the mounting rim 82".

During a surgical procedure to implant the femoral component 12 of FIG. 6 to the surgically-prepared distal end of the patient's femur, the cement pockets 70, 72, 74, 76, 78 are preloaded with bone cement. The femoral component 12 is then positioned on the patient's surgically-prepared distal femur, which has also been coated in bone cement. The angled arrangement of the cement pockets 70, 78 hydraulically loads the bone cement within the cement pockets 70, 78. This enhances containment of the bone cement and reduces the occurrences of cement plowing. This also improves filling of the bone cement and pressurization which, in turn, leads to enhanced bonding of the femoral component 12 to the distal femur.

It should be appreciated that although the embodiment of FIG. 6 illustratively shows both the posterior cement pocket 70 and the anterior cement pocket 78 being angled, it should be appreciated that other embodiments are also contemplated. For example, as shown in FIGS. 1-5, the femoral component 12 may be embodied with only the posterior cement pocket 70 being angled. Alternatively, the femoral component 12 may be embodied with only the anterior cement pocket 78 being angled.

Figure 7:
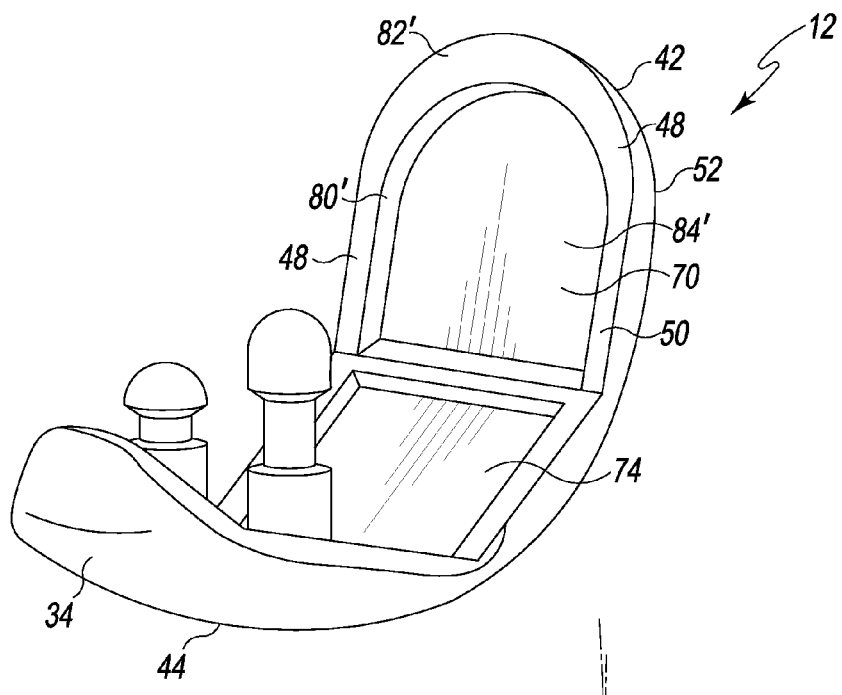
FIG. 7 is a perspective view of a unicompartmental femoral component.
Figure 8:
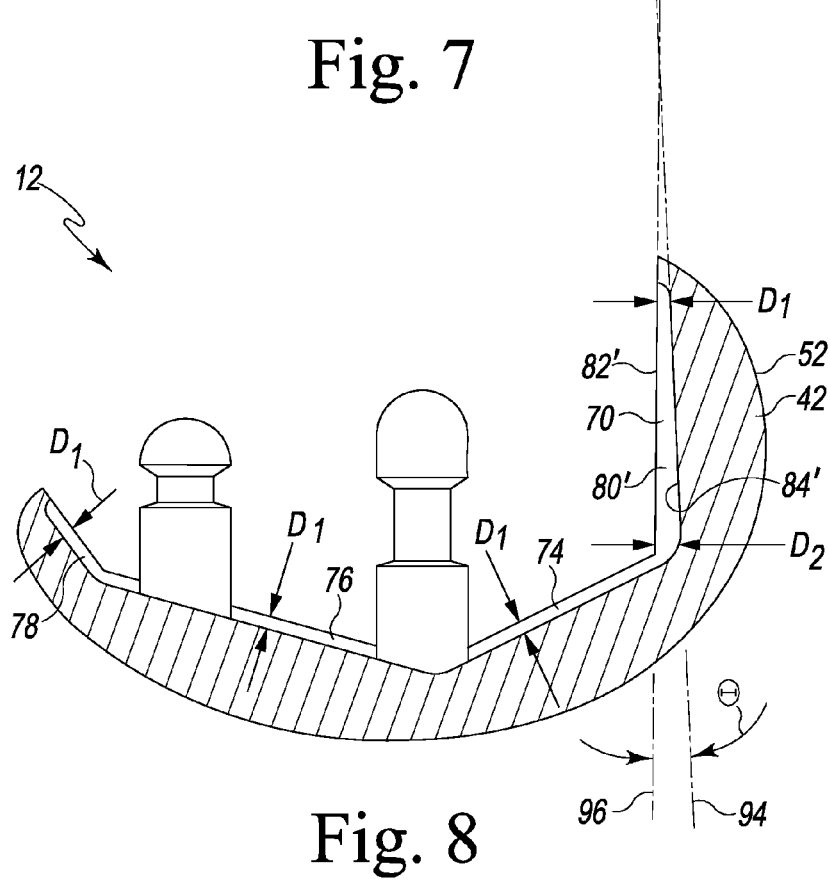
FIG. 8 is a sagittal cross sectional view of the unicompartmental femoral component of FIG. 7.

Referring now to FIGS. 7 and 8, the femoral component 12 may also be embodied as a unicompartmental femoral component. Like the other embodiments described herein, the posterior cement pocket 70 of the unicompartmental femoral component 12 may be angled. The angled arrangement of posterior cement pocket 70 hydraulically loads the bone cement within the cement pocket. This enhances containment of the bone cement and reduces the occurrences of cement plowing. The arrangement of the posterior cement pocket 70 also improves filling of the bone cement and pressurization which, in turn, leads to enhanced bonding of the unicompartmental femoral component 12 to the distal femur.

Figure 9:
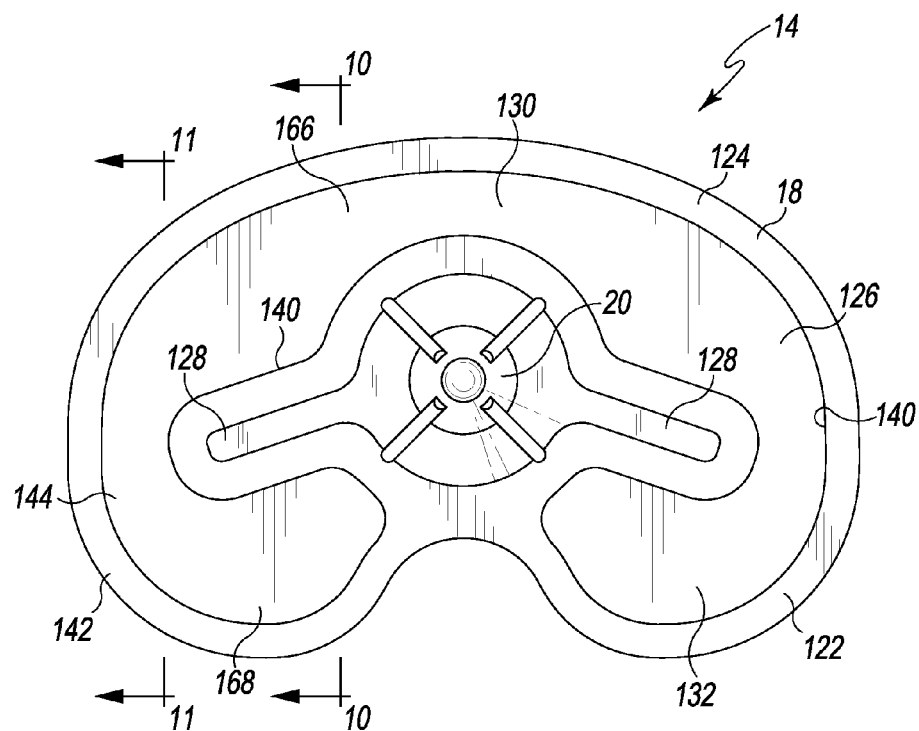
FIG. 9 is a plan view of the inferior side of the tibial tray of the knee prosthesis of FIG. 1.
Figure 10:
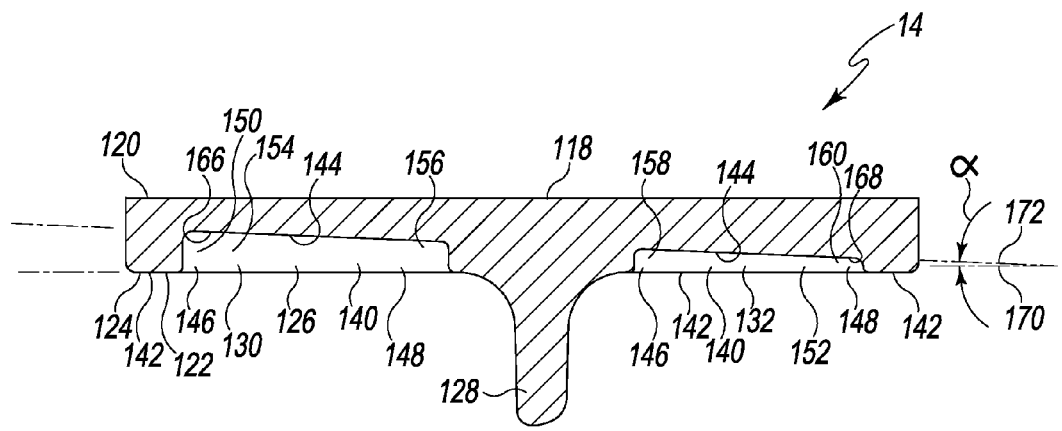
FIG. 10 is a sagittal cross section view of the tibial tray taken along the line 10-10 of FIG. 9, as viewed in the direction of the arrows.
Figure 11:
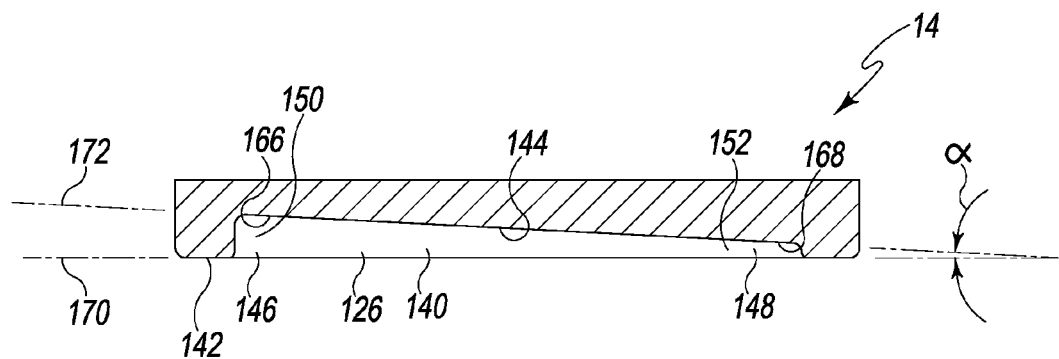
FIG. 11 is a sagittal cross section view of the tibial tray taken along the line 11-11 of FIG. 9, as viewed in the direction of the arrows.

Referring now to FIGS. 9-11, the concepts of the present disclosure may also be used in the design of a tibial component such as the tibial tray 14 of FIGS. 1 and 2. As shown in FIG. 10, a flat planar surface 118 is formed in the superior side 120 of the tibial tray 14. Specifically, the superior surface 118 of the tibial tray's platform 18 defines a smooth planar surface on which the bearing 16 of the knee prosthesis 10 is free to rotate when the bearing's stem 22 (see FIG. 2) is positioned within the complementary bore 24 (see FIG. 2) of the tibial tray 14. In other embodiments, the superior surface 118 of the tibial tray's platform 18 may be embodied with one or more features on which the bearing 16 may be snap-fit or otherwise secured to the tibial tray 14. In such a way, the bearing 16 is fixed relative to the tibial tray 14 (i.e., it is not rotative or moveable in the anterior/posterior or medial/lateral directions).

The tibial tray's inferior side 122 is opposite its superior side 120, and is the side of the tibial tray 14 that contacts the surgically-prepared proximal tibia of the patient. The elongated stem 20 extends inferiorly away from the tibial tray's inferior side 122. The tibial tray's inferior side 122 includes multiple surfaces that mate with planar surfaces surgically cut into the patient's proximal tibia. Specifically, as shown in FIGS. 9 and 10, an inferior fixation surface 124 extends generally in the transverse plane (i.e., in the direction of the anatomical transverse plane).

The inferior fixation surface 124 has a cement pocket 126 formed therein. In the illustrative embodiment described herein, the tibial tray's fins 128 divide the cement pocket 126 into separate cement pockets at various locations along the tray's medial/lateral width. In particular, an anterior cement pocket 130 is positioned anteriorly of the tray's fins 128 with a posterior cement pocket 132 being positioned posteriorly of the tray's fins 128. However, since the fins 128 do not stretch to the medial and lateral edges of the tray 14, the cement pockets 130, 132 are contiguous with one another such that a single, continuous cement pocket 126 is formed in the inferior side 122 of the tibial tray 14. It should be appreciated; however, that the tibial tray 14 could be embodied with one or more separate cement pockets.

Each of the cement pockets 126, 130, 132 is formed by a sidewall 140 that extends superiorly away from a mounting rim 142. As can be seen in FIGS. 9-11, the sidewall 140 forms the perimeter of the respective cement pockets 126, 130, 132. A top wall 144 is spaced apart from the mounting rim 142 and is connected thereto by the sidewall 140. In such a way, the sidewall 140 and the top wall 144 collectively define the respective cement pockets 126, 130, 132.

The cement pocket 126 is angled and, as a result, deeper at its anterior end than on its posterior end. In particular, when viewed sagittally, such as in the cross sectional view of FIGS. 10 and 11, the anterior end 146 of the sidewall 140 is wider than the posterior end 148 of the sidewall 140. As a result, the cement pocket 126 is deeper at its anterior end 150 than at its posterior end 152. Because the individual cement pockets formed by the fins 128 (i.e., the anterior cement pocket 130 and the posterior cement pocket 132) are, in essence, "sub-pockets" of the larger cement pocket 126, each of the cement pockets 130, 132 has a similar arrangement in which their respective anterior ends are deeper than their respective posterior ends. In particular, the anterior end 154 of the anterior cement pocket 130 is deeper than its posterior end 156. Likewise, the anterior end 158 of the posterior cement pocket 132 is deeper than its posterior end 160.

Such an arrangement creates an angled top wall 144. In particular, the top wall 144 slopes inferiorly from its anterior end 166 to its posterior end 168. This sloped arrangement is illustratively shown in the cross sectional views of FIGS. 10 and 11. As can be seen in that view, an imaginary plane 170 is defined by the mounting rim 142 of the inferior fixation surface 124, whereas the top wall 144 of the inferior fixation surface 124 defines an imaginary plane 172. The two imaginary planes 170, 172 form an acute angle ($\alpha$) therebetween. Such an acute angle is indicative of the slope of the top wall 144 relative to the mounting rim 142.

During a surgical procedure to implant the tibial tray 14 to the surgically-prepared proximal end of the patient's tibia, the cement pocket 126 is preloaded with bone cement. The tibial tray 14 is then positioned on the patient's surgically-prepared proximal tibia, which has also been coated in bone cement. The angled arrangement of cement pocket 126 hydraulically loads the bone cement within the cement pocket. This enhances containment of the bone cement and reduces the occurrences of cement plowing. The arrangement of the cement pocket 126 also forces any excess bone cement out the anterior side of the tibial tray 14 where it can be readily wiped away or otherwise removed by the surgeon.

Figure 12:
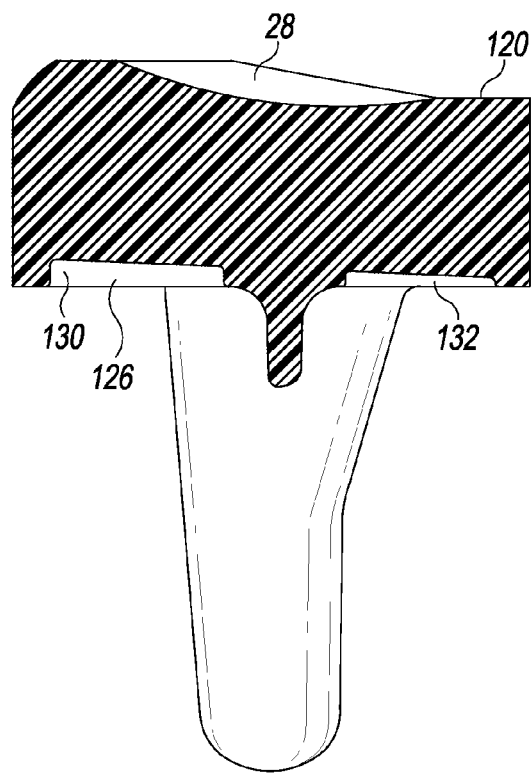
FIG. 12 is cross section view of an all-poly tibial component.

Referring now to FIG. 12, the tibial component may also be embodied as an all-poly tibial component. That is, in lieu of a modular design in which the tibial tray and the bearing are embodied as separate components, the concepts of the present disclosure may be utilized in the design of a monolithic polymeric tibial component. In such a case, the lateral articular surface 26 and the medial articular surface 28 configured to articulate with a lateral condyle surface 30 and a medial condyle surface 32 of the femoral component 12, respectively, are formed in the superior side 120 of the tibial component. Like the tibial tray 14 described herein, the cement pocket 126 of the all-poly tibial component of FIG. 12 may be angled. The angled arrangement of cement pocket 126 hydraulically loads the bone cement within the cement pocket and forces any excess bone cement out the anterior side of the all-poly tibial component where it can be readily wiped away or otherwise removed by the surgeon.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure as defined by the appended claims.

The invention claimed is:

1. An implantable orthopaedic knee prosthesis, comprising:
   a femoral component configured to be coupled to a surgically-prepared distal femur, the femoral component having (i) an articular side comprising a posterior femoral condyle surface, and (ii) a fixation side that is opposite the articular side, the fixation side comprising a fixation surface,
   wherein, when viewed in the sagittal plane, the fixation surface comprises (i) a peripheral rim, (ii) an angled bottom wall spaced apart posteriorly from the peripheral rim, and (iii) a superior wall extending posteriorly from the peripheral rim to the angled bottom wall,
   wherein the superior wall extends between a pair of sidewalls that extend inferiorly and superiorly on a medial side and a lateral side of the fixation surface, and the superior wall, the angled bottom wall, and the pair of sidewalls collectively define a cement pocket, and
   wherein, when viewed in the sagittal plane, (i) an imaginary plane defined by the peripheral rim forms an acute angle with an imaginary plane defined by the angled bottom wall such that the cement pocket is deeper at its inferior end than at its superior end, and (ii) the cement pocket has a depth at its superior end that is greater than zero millimeters.

2. The implantable orthopaedic knee prosthesis of claim 1, wherein, when viewed sagittally, an inferior end of each sidewall is wider than a corresponding superior end.

3. The implantable orthopaedic knee prosthesis of claim 1, wherein the fixation surface is a posterior fixation surface.

4. The implantable orthopaedic knee prosthesis of claim 1, wherein the fixation surface is a posterior chamfer fixation surface.

5. The implantable orthopaedic knee prosthesis of claim 1, wherein the articular side comprises a posterior lateral femoral condyle surface.

6. The implantable orthopaedic knee prosthesis of claim 1, wherein the articular side comprises a posterior medial femoral condyle surface.

7. An implantable orthopaedic knee prosthesis, comprising:
   a tibial tray configured to be coupled to a surgically-prepared proximal tibia,
   a bearing coupled to the tibial tray, the bearing having a medial articular surface and a lateral articular surface, and
   a femoral component configured to be coupled to a surgically-prepared distal femur, the femoral component having (i) a lateral condyle surface configured to articulate with the lateral articular surface of the bearing and a medial condyle configured to articulate with the medial articular surface of the bearing, (ii) a lateral fixation surface opposite the lateral condyle surface, and (iii) a medial fixation surface opposite the medial condyle surface,
   wherein, when viewed in the sagittal plane, the medial fixation surface comprises (i) a medial peripheral rim, (ii) a medial angled bottom wall spaced apart posteriorly from the medial peripheral rim, and (iii) a medial superior wall extending posteriorly from the medial peripheral rim to the medial angled bottom wall,
   wherein the medial superior wall extends between a pair of medial sidewalls that extend inferiorly and superiorly on a medial side and a lateral side of the medial fixation surface, and the medial superior wall, the medial angled bottom wall, and the pair of medial sidewalls collectively define a medial cement pocket,
   wherein, when viewed in the sagittal plane, an imaginary plane defined by the medial peripheral rim forms an acute angle with an imaginary plane defined by the medial angled bottom wall such that the medial cement pocket is deeper at its inferior end than at its superior end, and (ii) the medial cement pocket has a depth at its superior end that is greater than zero millimeters,
   wherein, when viewed in the sagittal plane, the lateral fixation surface comprises (i) a lateral peripheral rim, (ii) a lateral angled bottom wall spaced apart posteriorly from the lateral peripheral rim, and (iii) a lateral superior wall extending posteriorly from the lateral peripheral rim to the lateral angled bottom wall,
   wherein the lateral superior wall extends between a pair of lateral sidewalls that extend inferiorly and superiorly on a medial side and a lateral side of the lateral fixation surface, and the lateral superior wall, the lateral angled bottom wall, and the pair of lateral sidewalls collectively define a lateral cement pocket, and
   wherein, when viewed in the sagittal plane, an imaginary plane defined by the lateral peripheral rim forms an acute angle with an imaginary plane defined by the lateral angled bottom wall such that the lateral cement pocket is deeper at its inferior end than at its superior end, and (ii) the lateral cement pocket has a depth at its superior end that is greater than zero millimeters.

8. The implantable orthopaedic knee prosthesis of claim 7, wherein, when viewed sagittally, an inferior end of each medial sidewall of the medial fixation surface is wider than its corresponding superior end.

9. The implantable orthopaedic knee prosthesis of claim 7, wherein, when viewed sagittally, an inferior end of each lateral sidewall of the lateral fixation surface is wider than its corresponding superior end.

10. An implantable orthopaedic knee prosthesis, comprising:
    a femoral component configured to be coupled to a surgically-prepared distal femur, the femoral component having (i) an articular side comprising a femoral condyle surface, and (ii) a fixation side that is opposite the articular side, the fixation side comprising a fixation surface, wherein the fixation surface has a cement pocket formed therein, the cement pocket is deeper at its inferior end than at its superior end, wherein the cement pocket is partially defined by an angled bottom wall that extends from the inferior end to the superior end and a superior wall extending posteriorly from a peripheral rim to the angled bottom wall, the superior wall extending between a pair of sidewalls that extend inferiorly and superiorly on a medial side and a lateral side of the fixation surface, and the cement pocket has a depth at the superior wall that is greater than zero millimeters, wherein, when viewed sagittally, an imaginary plane defined by the peripheral rim forms an acute angle with an imaginary plane defined by the angled bottom wall.

11. The implantable orthopaedic knee prosthesis of claim 10, wherein:

the fixation surface comprises a posterior fixation surface having a posterior cement pocket formed therein.

12. The implantable orthopaedic prosthesis of claim 10, wherein the fixation surface is a posterior fixation surface.

13. The implantable orthopaedic prosthesis of claim 10, wherein the fixation surface is a posterior chamfer fixation surface.

14. The implantable orthopaedic knee prosthesis of claim 10, wherein the femoral component comprises a unicompartmental femoral component.

* * * * *